United States Patent
Huang et al.

(10) Patent No.: US 11,813,028 B2
(45) Date of Patent: Nov. 14, 2023

(54) ACTIVE-DETECTION SELF-PROPELLED ARTIFICIAL INTELLIGENCE SURGICAL NAVIGATION CART

(71) Applicant: EPED, Inc., Kaohsiung (TW)

(72) Inventors: Ta-Ko Huang, Kaohsiung (TW); Jerry T. Huang, Kaohsiung (TW)

(73) Assignee: EPED, Inc., Kaohsiung (TW)

( * ) Notice: Subject to any disclaimer, the term of this patent is extended or adjusted under 35 U.S.C. 154(b) by 952 days.

(21) Appl. No.: 16/586,869

(22) Filed: Sep. 27, 2019

(65) Prior Publication Data

US 2020/0100846 A1 Apr. 2, 2020

(30) Foreign Application Priority Data

Sep. 27, 2018 (TW) ................................ 107134160
Nov. 26, 2018 (TW) ................................ 107142117

(51) Int. Cl.
*A61B 34/30* (2016.01)
*A61B 34/20* (2016.01)
*B62B 5/00* (2006.01)
*A61B 6/00* (2006.01)
*A61B 50/13* (2016.01)
*A61B 90/98* (2016.01)
*A61B 17/00* (2006.01)
*A61B 34/00* (2016.01)
*A61B 17/072* (2006.01)

(52) U.S. Cl.
CPC ............ *A61B 34/20* (2016.02); *A61B 6/4458* (2013.01); *A61B 50/13* (2016.02); *A61B 90/98* (2016.02); *B62B 5/0033* (2013.01); *B62B 5/0076* (2013.01); *A61B 17/072* (2013.01); *A61B 34/30* (2016.02); *A61B 34/71* (2016.02); *A61B 2017/00212* (2013.01); *A61B 2034/2055* (2016.02)

(58) Field of Classification Search
CPC ......... A61B 34/10; A61B 34/20; A61B 34/30; A61B 34/71; A61B 46/10; A61B 50/10; A61B 50/13; A61B 17/072; A61B 17/7089; A61B 90/98; A61B 6/4458; A61B 34/70
USPC ........... 227/19, 175.1; 606/1, 130, 139, 219; 700/218; 312/209
See application file for complete search history.

(56) References Cited

U.S. PATENT DOCUMENTS

| | | | | |
|---|---|---|---|---|
| 9,364,955 | B2 * | 6/2016 | Oyola | A61B 34/71 |
| 9,526,920 | B2 * | 12/2016 | Tanis | A61N 7/00 |
| 9,718,188 | B2 * | 8/2017 | Stubbs | G06Q 10/087 |
| 9,796,529 | B1 * | 10/2017 | Hoareau | G05D 1/0282 |
| 9,827,683 | B1 * | 11/2017 | Hance | B65G 1/065 |

(Continued)

*Primary Examiner* — Scott A Smith
(74) *Attorney, Agent, or Firm* — Schmeiser, Olsen & Watts LLP

(57) ABSTRACT

An active detection self-propelled artificial intelligence surgery navigation cart applied in medical institutes includes a cart body, a control unit, a signal transmission unit, a detection unit, a robotic arm and/or an optical navigation host. The cart can travel to a designated place or follow a counterpart (based on a stored map path) according to a predetermined schedule or an inputted instruction, or the cart can be controlled by an external remote control system or a counterpart to be followed, so as to achieve the effect of reducing the burden of medical staff while they are walking around, so that the medical staff can concentrate on the care of patients or improve the quality of surgical operations.

12 Claims, 4 Drawing Sheets

(56) References Cited

U.S. PATENT DOCUMENTS

| | | | | |
|---|---|---|---|---|
| 2001/0035702 A1* | 11/2001 | Murphy | ............... | A61B 50/10 |
| | | | | 312/285 |
| 2004/0249673 A1* | 12/2004 | Smith | ............... | A61B 5/02055 |
| | | | | 705/2 |
| 2009/0000627 A1* | 1/2009 | Quaid | ............... | A61N 1/3605 |
| | | | | 128/898 |
| 2012/0305787 A1* | 12/2012 | Henson | ............... | A61L 2/10 |
| | | | | 250/492.1 |
| 2015/0032252 A1* | 1/2015 | Galluzzo | ............... | B60P 1/5423 |
| | | | | 700/218 |
| 2015/0100066 A1* | 4/2015 | Kostrzewski | ............... | A61B 34/30 |
| | | | | 606/130 |
| 2015/0223897 A1* | 8/2015 | Kostrzewski | ............... | A61B 46/10 |
| | | | | 606/1 |
| 2015/0374446 A1* | 12/2015 | Malackowski | ............... | A61B 34/10 |
| | | | | 606/130 |
| 2017/0112954 A1* | 4/2017 | Dayton | ............... | A61L 9/20 |
| 2017/0252114 A1* | 9/2017 | Crawford | ............... | A61B 17/7089 |
| 2017/0300654 A1* | 10/2017 | Stein | ............... | H01Q 1/42 |
| 2018/0132966 A1* | 5/2018 | Désaulniers | ............... | A61B 90/50 |
| 2020/0100846 A1* | 4/2020 | Huang | ............... | G05B 19/18 |

\* cited by examiner

ACTIVE-DETECTION SELF-PROPELLED ARTIFICIAL INTELLIGENCE SURGICAL NAVIGATION CART

FIELD OF INVENTION

The present disclosure relates to the field of self-propelled carts, in particular to an active detection self-propelled artificial intelligence surgery navigation cart applied in the medical field.

BACKGROUND OF INVENTION

Description of the Related Art

In hospitals or medical centers, doctors or nurses need an extensive use of carts for placing and moving medical supplies or instruments, or even carrying out the administration work of a medical system such as transferring medical records, regardless of their giving medical consultation, patrolling rooms, and performing surgical operation, and medical staff may push these carts and carry the medical supplies and instruments with them during work.

For instance, when a nurse of a hospital changes the medicines for patients regularly, the nurse needs to push the cart loaded with the required medicines and related medical instruments to each ward for regular inspection, and such cart may carry a large quantity of medicines and medical instruments, so that the pushing process requires a lot of physical strength and attention. However, the heavy medical work of handing a large amount of medicines and medical instruments and pushing the cart is definitely a burden on the consumption of medical labor. If we can save or minimize such labor, we will be able to put the whole medical labor force into medical treatments and it will be a big help to reduce the workload of the medical staff. Therefore, the present disclosure provides a medical cart capable of following the medical staff around automatically, so as to overcome the aforementioned issue effectively by reducing the consumption of medical labor.

SUMMARY OF THE INVENTION

It is a primary objective of the present disclosure to provide an active detection self-propelled artificial intelligence surgery navigation cart to overcome the aforementioned drawbacks of the prior art.

To achieve the aforementioned and other objectives, this disclosure provides a cart comprising a cart body, a control unit, a signal transmission unit and a detection unit, wherein the cart body has at least one storage space and a travelling device to achieve the effects of driving the cart and storing objects; the control unit is installed in the cart body and telecommunicatively coupled to the travelling device of the cart body, and the control unit is provided for transmitting a travel instruction to the travelling device, so that the cart can move; the signal transmission unit is also installed in the cart body and telecommunicatively coupled to the control unit for receiving and transmitting an external control signal to the control unit; the detection unit is also installed in the cart body and telecommunicatively coupled to the control unit for actively and continuously detecting whether there is a corresponding external counterpart and returning a corresponding message to the control unit to perform the action when the counterpart of the cart is detected.

As described above, the active detection self-propelled artificial intelligence surgery navigation car of the present disclosure adopts an active detection unit to keep detecting whether there is an external counterpart corresponding to the cart through an RFID or infrared detection. After the counterpart of the cart is detected, a signal will be fed back to the control unit of the cart, and when the control unit receives and matches the signal, the cart will follow the counterpart actively.

The cart may control the required corresponding counterpart and its moving path and starting time by a remote message and the signal transmission unit is provided for inputting/outputting the control signal, so that when the signal transmission unit receives the external control signal and transmits the control signal to the control unit, the cart will actively base on the data for following the counterpart, following the time, and starting the path according to the control signal, or the cart is actively driven to the specific time, and place, and after the active following action is matched, the cart will actively follow the counterpart. Wherein, the external signal is transmitted via wireless transmission such as WIFI, Bluetooth, infrared or NFC transmission.

If a large quantity of robotic arms are installed to the related machine, the construction cost will be very high, so that the medical robotic arm is installed to the active detection self-propelled artificial intelligence surgery navigation cart of the present disclosure in such a way to allow the medical robotic arm to be used flexibly in different clinic rooms or operating rooms in order to improve the scheduling flexibility of the robotic arm while avoiding the failure of moving the robotic arm by the medical staff due to the heavy weight of the robotic arm. To minimize the risk of damaging the robotic arm while it is moving, the robotic arm has at least one anti-collision detector for detecting obstacles around the robotic arm.

Wherein, the anti-collision detector is installed at a joint of the robotic arm. If the anti-collision detector detects an approaching object, the anti-collision detector will send a control signal to drive the robotic arm to change its posture for avoidance. If the active detection self-propelled artificial intelligence surgery navigation cart follows a medical staff or a counterpart and the anti-collision detector of the robotic arm detects a signage or any other object that may hit the robotic arm, the robotic arm will automatically make a movement to avoid the possible collision caused by the object.

In addition, the active detection self-propelled artificial intelligence surgery navigation cart may be controlled by a control system through an external signal, wherein after the control system outputs the aforementioned external control signal to the signal transmission unit, the control system transmits the external control signal to the control unit to control the operation of the cart. Further, the control system can control the operation of a plurality of carts simultaneously.

The application of the active detection self-propelled artificial intelligence surgery navigation cart of this disclosure provides the following functions:

(1) Self-propelled Function: The cart actively bases on the data to set different operating modes of following a counterpart, following a certain time, or starting a path according to the control signal, and these operating modes include the modes for specific time and place, automatically set in place, return-programming or ground guide line detection-no programming, etc., and the return-programming refers to the action of stopping the operation at a place when hampered and then resetting the cart to its original position for a restart or continuing the operation at the place where it stopped.

(2) Active Follow Function: After a counterpart of the cart is detected, the detection signal is fed back to the control unit of the cart, and after the control unit receives and matches the signal, the cart will actively follow the counterpart. Wherein the counterpart is a device with a signal source, such as a hospital bed or a wearable device for synchronous movement.

(3) Tracking Function: The robotic arm has a connecting arm or a suspension arm with an automatic control device capable of actively detecting and moving a navigation system to track a reflective element to obtain the best optical signal, to facilitate surgical operations.

To lower the replacement fees of current medical carts, the active detection self-propelled artificial intelligence surgery navigation cart further comprises a coupling mechanism installed onto an outer side of the cart body for connecting an external cart device, so that hospitals no longer need to replace all current carts, but simply use the coupling mechanism to combine the current carts with the active detection self-propelled artificial intelligence surgery navigation cart of the present disclosure to achieve the effect of automatically following a counterpart or moving the carts to a destination. When the robotic arm is installed to the original carts of the hospital, the system of the control unit of the present disclosure is independent to the cart navigation system installed with the robotic arm, and each system will have the following functions:

(1) Self-propelled Function. This function is substantially the same as the aforementioned operating modes of automatically set in place, return-programming or ground guide line detection-no programming, etc.

(2) Active Follow Function: This function is to follow a device with a signal source such as a hospital bed or a wearable device for synchronous movement or provide a follow function between the cart and such device.

(3) Tracking Function: The connecting arm or suspension arm has an automatic control device capable of detecting and moving the navigation system to track a reflective element, so as to obtain the best optical signal.

In this separate system, the carts may be operated independently or jointly according to the surgical requirements or different departments and directly assigned to go to a corresponding location (such as Room A with an optical navigation system or Room B with a robotic arm navigation system).

DESCRIPTION OF THE PREFERRED EMBODIMENTS

To make it easier for our examiner to understand the technical content of the disclosure, we use preferred embodiments together with the attached drawings for the detailed description of the disclosure.

Figure 1:
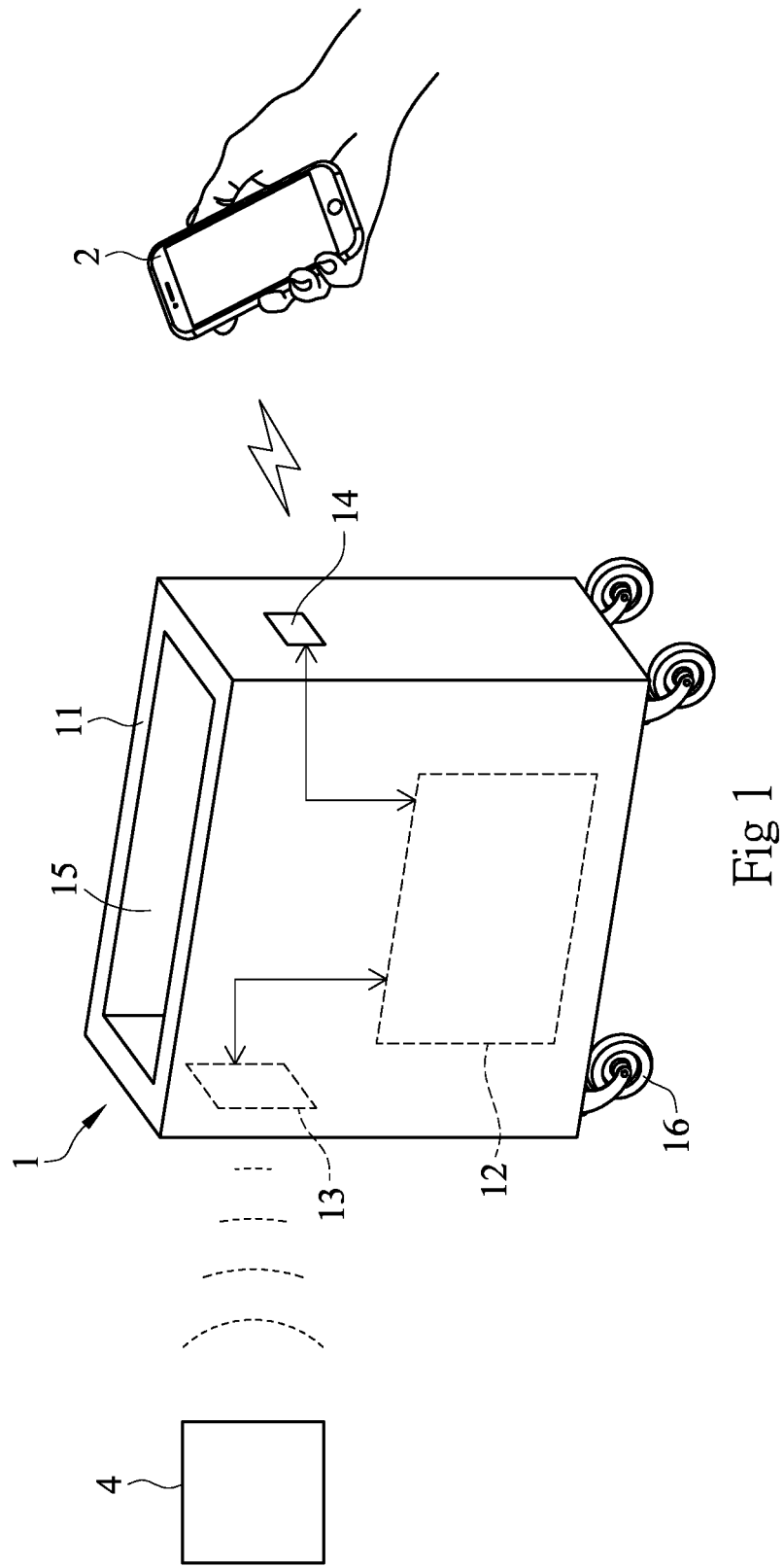
FIG. 1 is a schematic view of an active detection self-propelled artificial intelligence surgery navigation cart in accordance with a first embodiment of this disclosure.

With reference to FIG. 1 for a perspective view of an active detection self-propelled artificial intelligence surgery navigation cart in accordance with the first embodiment of this disclosure, the active detection self-propelled artificial intelligence surgery navigation cart 1 comprises a cart body 11, a control unit 12, a signal transmission unit 13 and a detection unit 14. The cart body 11 has at least one storage space 15 and a travelling device 16. It is noteworthy that the storage space 15 is just an implementation mode. This disclosure is not limited to such implementation mode only, but any device with a pull basket or transverse compartment is also referred to as the storage space 15 of the present disclosure. The travelling device 16 is a device capable of moving the cart 1 such as a device having a set of wheels driven by an electric motor or a set of magnetic levitation devices, or a device using aerodynamics to move the cart 1. The control unit 12 is installed to the cart body 11 for controlling the operation of the cart body 11. The signal transmission unit 13 is installed to the cart body 11 and telecommunicatively coupled to the control unit 12 for receiving a control signal and transmitting the control signal to the control unit 12. The detection unit 14 is installed to the cart body 11 and telecommunicatively coupled to the control unit 12 for detecting an actuating counterpart 2 of the cart and returning the detection result to the control unit 12. In addition, the cart body 11 has an instrument platform for loading equipment and placing the required surgical instruments, or carrying mobile scanners or X-ray machines.

In this embodiment, the active detection self-propelled artificial intelligence surgery navigation cart 1 includes two active follow methods as described below.

The first method uses the detection unit 14 of the cart to actively scan its actuating counterpart 2, and then returning a corresponding signal to the control unit 12 for a matched link, and finally moving actively according to the position of the actuating counterpart 2 after the cart 1 is linked. Wherein, the active scan is achieved by a RFID or infrared detection technology, and the actuating counterpart 2 is a RFID card, a handheld communication device, a handheld computer or a special corresponding device provided for the detection unit 14 to complete the matching operation.

The second method uses the signal transmission unit 13 to transmit an external control signal to the control unit 12 when the external control signal is transmitted by the control system 4 to the cart 1 via wireless transmission, and the control unit 12 can use the parameters such as the information of time, place, counterpart, etc. of the control signal to drive the cart 1 to a place at a specific time to match with the counterpart. Wherein, the external control signal is transmitted via a WIFI, Bluetooth, Infrared or NFC transmission.

Figure 2:
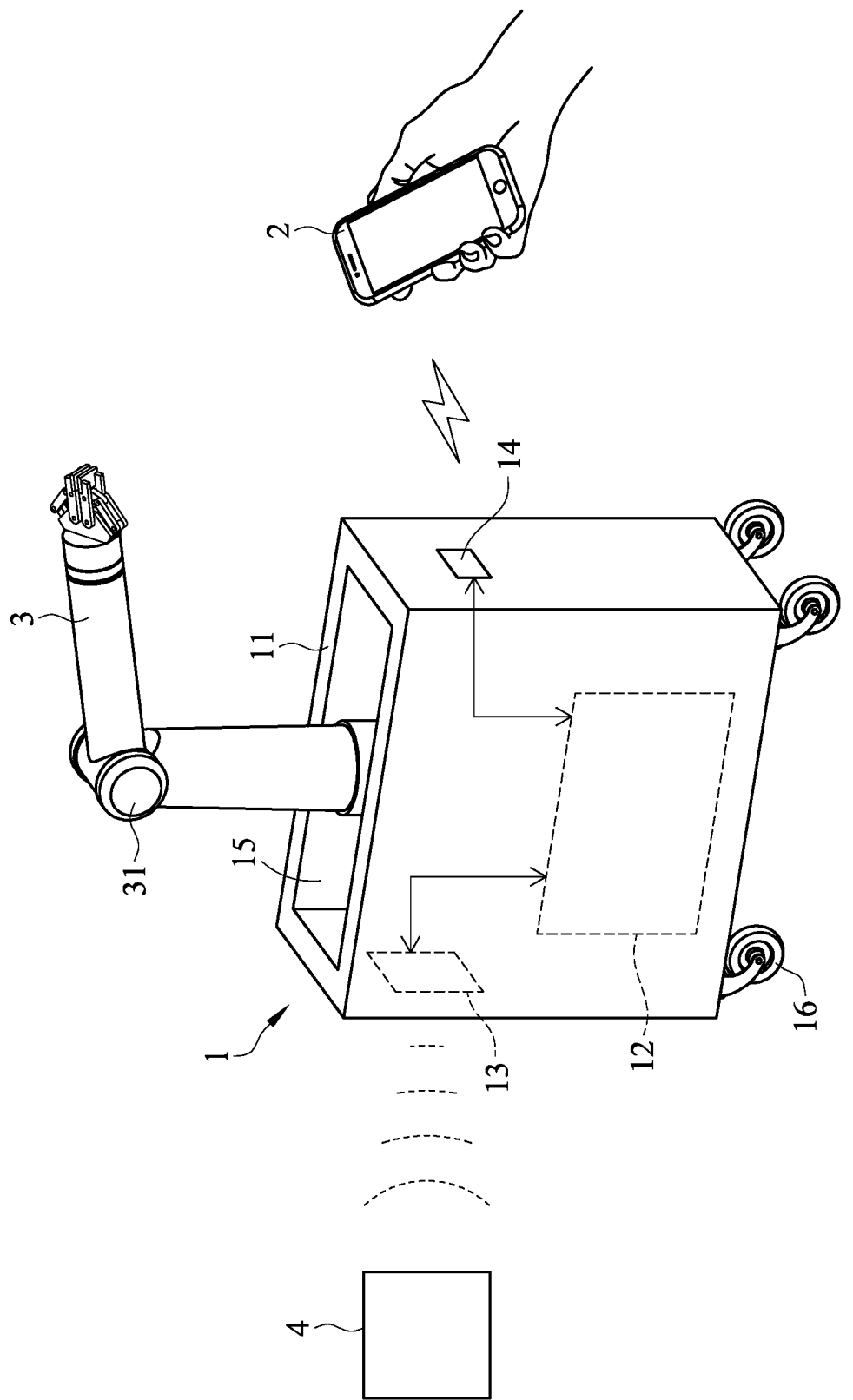
FIG. 2 is a schematic view of an active detection self-propelled artificial intelligence surgery navigation cart in accordance with a second embodiment of this disclosure.

With reference to FIG. 2 for a perspective view of an active detection self-propelled artificial intelligence surgery navigation cart in accordance with the second embodiment of the present disclosure, the second embodiment is substantially the same as the first embodiment, except the second embodiment has a medical robotic arm 3 installed onto the cart. Wherein, the robotic arm 3 has at least one anti-collision detector 31, and the anti-collision detector 31 of this embodiment is installed at a joint of the robotic arm 3, but this disclosure is not limited to such arrangement only, and the installation position of the anti-collision detector 31 may be adjusted to appropriately according to the arms of different models. If the active detection self-propelled artificial intelligence surgery navigation cart 1 of this embodiment is travelling and detects a foreign object such as a signage disposed at a ceiling or on a wall, which may collide with the anti-collision detector 31 in a traveling path, then the anti-collision detector 31 will return a signal to the control unit 12 to control the operation of the medical robotic arm 3 in order to avoid the collision by the foreign object or any damage caused by the collision. If the self-propelled function is enabled and the cart body has built-in map information to move along a planned moving path, such as the best plannable moving path (including the shortest path, the path with least obstacles, or the most suitable elevator selected according to the dimensions of the carried object, etc.) to give the best automation or artificial intelligence of the cart.

Figure 3:
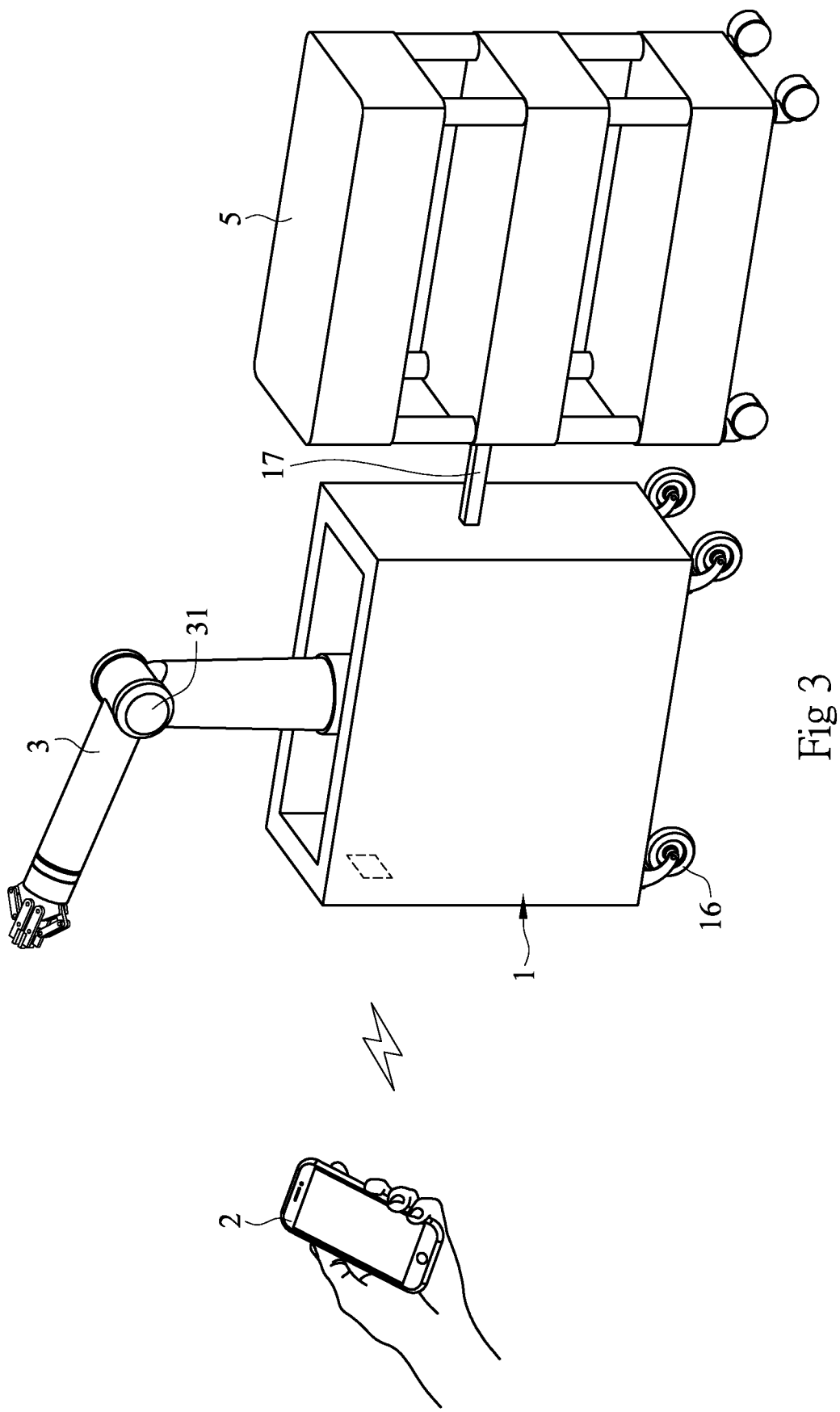
FIG. 3 is a schematic view of an active detection self-propelled artificial intelligence surgery navigation cart in accordance with a third embodiment of this disclosure.

With reference to FIG. 3 for a perspective view of an active detection self-propelled artificial intelligence surgery navigation cart in accordance with the third embodiment of the present disclosure, the active detection self-propelled artificial intelligence surgery navigation cart is integrated with the using mode of the conventional cart. As described above, the operation of the third embodiment is substantially the same as that of the first embodiment, except the cart of the third embodiment further comprises a coupling mechanism 17 installed to an outer side of the cart body 11 for coupling an external cart device 5. When the cart 1 of the present disclosure performs the active following action, the external cart device 5 also performs the same action due to the coupling, and the coupling mechanism 17 is telecommunicatively coupled to the control unit 12, and the control unit 12 issues a signal to control the coupling mechanism 17 to perform the coupling operation or further comprises an image capture device for capturing an image of the coupling mechanism 17 when moving to timely adjust the coupling position of the coupling mechanism 17 with another cart, so as to achieve the effect of coupling a plurality of carts.

Figure 4:
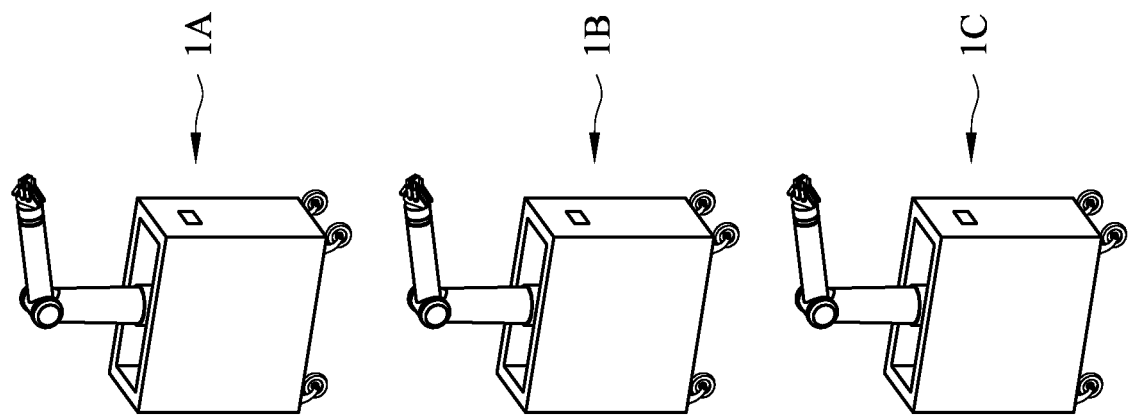
FIG. 4 is a schematic view showing the correspondence between the active detection self-propelled artificial intelligence surgery navigation carts and a control system in accordance with an embodiment of the present disclosure.
Figure 4:
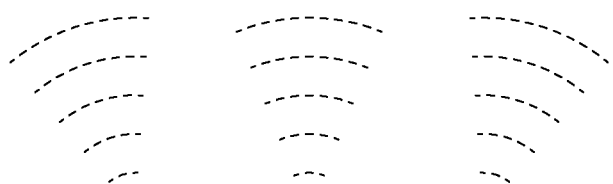
Figure 4:
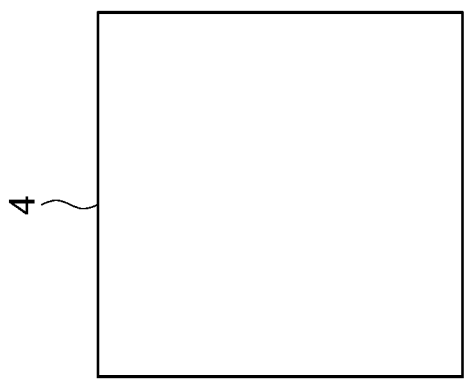

With reference to FIG. 4 for a schematic view showing the correspondence between the active detection self-propelled artificial intelligence surgery navigation cart and a control system in accordance with an embodiment of the present disclosure, the active detection self-propelled artificial intelligence surgery navigation cart 1 corresponds to a control system 4 through the external signal, and the control system 4 inputs the aforementioned external control signal to the signal transmission unit 13 and the control unit 12, and then the control unit 12 controls the operation of the cart 1. However, the control system 4 may not just correspond to one cart only, but can transmit the external control signal to a plurality of carts (1A, 1B, 1C) to control the moving path or assigned task of the plurality of carts simultaneously.

In addition, this embodiment further integrates the Visual SLAM technology by installing a Visual SLAM device to the cart (directly coupling the Visual SLAM device to the system of the cart) or a robotic arm (directly coupling the robotic arm to the system of the cart) or in a room (such as an operating room or a ward via network connection and message link with the cart). With the operation of a detector of the Visual SLAM device, the information of an instantly 3D scene may be created or the already created 3D scene may be received when the cart arrives and enters into the room, and such information is provided for the robotic arm of the cart and the optical navigation system having the capability of avoiding obstacles along the moving path. In other words, if any obstacle enters into the moving range of the robotic arm and the optical navigation system, the corresponding devices will stop their operations while detecting whether or not the obstacle can be eliminated, and then the corresponding devices will resume their operations, or the calculation of the aforementioned information may change the posture of the robotic arm or optical navigation system in order to continue traveling smoothly. Further, automatic calculations may be used to dodge the obstacle and set the corresponding devices at the best working angle or position to save the trouble of adjusting the position repeatedly by the medical staff. Further, the information of the created 3D scene may be sent to various connected autonomous devices synchronously to synchronize the movement and improve the efficiency. This arrangement not just overcomes the aforementioned drawbacks of the prior art related to the consumption of medical labor and the risk of damaging the equipment easily by improper operation only, but also minimizes the risk of injuring the doctors caused by the collision of the obstacle with the robotic arm or optical navigation system during a medical operation process. Besides the Visual-SLAM, different feedback or induction technologies may be integrated in order to autonomously avoid obstacles along the moving path or directly stop the operation to maintain safety and protecting the equipment connected to the cart body while the cart is travelling.

In summation, the, active detection self-propelled artificial intelligence surgery navigation cart operated independently or controlled and allocated by a unified system to achieve the self-propelled function, an active follow function, and a tracking function as described below:

Self-propelled Function: This function is to actively follow the counterpart or the information of time, or start moving along a path according to the control signal.

Active Follow Function: This function detects the counterpart of the cart and feeds back a corresponding signal to the control unit of the cart. After the control unit receives and matches the signal, the cart will actively follow the counterpart, wherein the counterpart is a device with a signal source, such as a hospital bed or a wearable device, etc. and the device will be operated synchronously.

Tracking Function: The connecting arm or suspension arm installed to the cart has an automatic control device to actively detect and move the navigation system to track a reflective element and compute the most appropriate location to obtain the best optical signal receiving positon to reduce the time for the doctors or nurses to make adjustments.

The system may be operated independently or jointly according to the surgical requirements or different departments to directly assign the corresponding carts to go to the corresponding location (such as Room A having an optical navigation system or Room B having a robotic arm navigation system). Further, the system may be used for moving related instruments or medical records to a designated place to achieve the effect of assisting the work of moving these instruments or medical records.

While the present disclosure has been described by means of specific embodiments, numerous modifications and variations could be made thereto by those skilled in the art without departing from the scope and spirit of the invention set forth in the claims.

What is claimed is:

1. An active detection self-propelled artificial intelligence surgery navigation cart, comprising:
a cart body, having at least one storage space and a travelling device;
a control unit, installed in the cart body, for controlling an operation of the cart body;
a signal transmission unit, installed in the cart body, and telecommunicatively coupled to the control unit, for receiving and transmitting a control signal to the control unit;

a detection unit, installed in the cart body, and telecommunicatively coupled to the control unit, for detecting an actuating counterpart of the cart and returning a detection result to the control unit, wherein, in turn, the control unit actively guides the self-propelled artificial intelligence surgery navigation cart to follow the counterpart by setting different operating modes of following the counterpart according to the control signal, including stopping an operation when the cart is hampered, resetting the cart to an original position, or continuing the operation; and a robotic arm, installed in the cart, and telecommunicatively coupled to the control unit, wherein the robotic arm comprises:
   a navigation system; and
   an automatic control device configured to actively detect and move the navigation system to track a reflective element in order to facilitate surgical operations.

2. The active detection self-propelled artificial intelligence surgery navigation cart as claimed in claim 1, wherein the robotic arm has at least one anti-collision detector.

3. The active detection self-propelled artificial intelligence surgery navigation cart as claimed in claim 2, wherein the anti-collision detector is installed at a joint of the robotic arm.

4. The active detection self-propelled artificial intelligence surgery navigation cart as claimed in claim 1, wherein the signal transmission unit transmits the signal via a wireless transmission.

5. The active detection self-propelled artificial intelligence surgery navigation cart as claimed in claim 1, wherein the cart is synchronized to a control system via a signal, and after the control system outputs a control signal to the signal transmission unit, the signal transmission unit transmits the control signal to the control unit to control the operation of the cart.

6. The active detection self-propelled artificial intelligence surgery navigation cart as claimed in claim 1, wherein the cart body further comprises a coupling mechanism installed on an outer side thereof and provided for linking another cart.

7. An active detection self-propelled artificial intelligence surgery navigation cart, comprising:
   a cart body, having at least one storage space and a travelling device;
   a control unit, installed in the cart body, for controlling an operation of the control unit;
   a signal transmission unit, installed in the cart body, and telecommunicatively coupled to the control unit, for receiving and transmitting a control signal to the control unit;
   a detection unit, installed in the cart body, and telecommunicatively coupled to the control unit, for detecting an actuating counterpart of the cart and returning a detection result to the control unit, wherein, in turn, the control unit actively guides the self-propelled artificial intelligence surgery navigation cart to follow the counterpart by setting different operating modes of following the counterpart according to the control signal, including stopping an operation when the cart is hampered, resetting the cart to an original position, or continuing the operation;
   a robotic arm, installed in the cart, and telecommunicatively coupled to the control unit, wherein the robotic arm comprises:
     a navigation system; and
     an automatic control device configured to actively detect and move the navigation system to track a reflective element in order to facilitate surgical operations; and
   an optical navigation system, installed in the cart, and telecommunicatively coupled to the control unit.

8. The active detection self-propelled artificial intelligence surgery navigation cart as claimed in claim 7, wherein the robotic arm has at least one anti-collision detector.

9. The active detection self-propelled artificial intelligence surgery navigation cart as claimed in claim 8, wherein the anti-collision detector is installed at a joint of the robotic arm.

10. The active detection self-propelled artificial intelligence surgery navigation cart as claimed in claim 7, wherein the signal transmission unit transmits the signal via a wireless transmission.

11. The active detection self-propelled artificial intelligence surgery navigation cart as claimed in claim 7, wherein the cart is synchronized to a control system via a signal, and after the control system outputs a control signal to the signal transmission unit, the signal transmission unit transmits the control signal to the control unit to control the operation of the cart.

12. The active detection self-propelled artificial intelligence surgery navigation cart as claimed in claim 7, wherein the cart body further comprises a coupling mechanism installed on an outer side thereof and provided for linking another cart.

\* \* \* \* \*